United States Patent
Poulsen et al.

(10) Patent No.: US 7,306,916 B2
(45) Date of Patent: Dec. 11, 2007

(54) METHODS FOR DETECTING CHROMOSOME ABERRATIONS

(75) Inventors: Tim Svenstrup Poulsen, Horsholm (DK); Susan Medom Poulsen, Horsholm (DK); Kenneth Heesche Petersen, Smorum (DK)

(73) Assignee: Dako Denmark A/S, Glostrup (DK)

( * ) Notice: Subject to any disclaimer, the term of this patent is extended or adjusted under 35 U.S.C. 154(b) by 165 days.

(21) Appl. No.: 11/119,755

(22) Filed: May 3, 2005

(65) Prior Publication Data
US 2006/0078904 A1   Apr. 13, 2006

Related U.S. Application Data

(60) Provisional application No. 60/567,440, filed on May 4, 2004, provisional application No. 60/567,570, filed on May 4, 2004.

(51) Int. Cl.
  C12Q 1/68 (2006.01)
  C07H 21/02 (2006.01)
  C07H 21/04 (2006.01)

(52) U.S. Cl. .......................... 435/6; 536/23.1; 536/24.2

(58) Field of Classification Search .................... 435/6; 536/23.1, 24.3
See application file for complete search history.

(56) References Cited

U.S. PATENT DOCUMENTS

| | | | |
|---|---|---|---|
| 5,527,675 A | 6/1996 | Coull et al. | |
| 5,539,082 A | 7/1996 | Nielsen et al. | |
| 5,623,049 A | 4/1997 | Lobberding et al. | |
| 5,714,331 A | 2/1998 | Buchardt et al. | |
| 5,736,336 A | 4/1998 | Buchardt et al. | |
| 5,750,340 A * | 5/1998 | Kim et al. ...................... | 435/6 |
| 5,766,855 A | 6/1998 | Buchardt et al. | |
| 5,773,571 A | 6/1998 | Nielsen et al. | |
| 5,786,461 A | 7/1998 | Buchardt et al. | |
| 5,837,459 A | 11/1998 | Berg et al. | |
| 5,891,625 A | 4/1999 | Buchardt et al. | |
| 5,972,610 A | 10/1999 | Buchardt et al. | |
| 5,986,053 A | 11/1999 | Ecker et al. | |
| 6,025,126 A * | 2/2000 | Westbrook ...................... | 435/6 |
| 6,107,470 A | 8/2000 | Nielsen et al. | |
| 6,201,103 B1 | 3/2001 | Nielsen et al. | |
| 6,228,982 B1 | 5/2001 | Norden et al. | |
| 6,357,163 B1 | 3/2002 | Buchardt et al. | |
| 6,414,133 B1 * | 7/2002 | Dietz-Band et al. ....... | 536/24.3 |
| 6,730,474 B1 * | 5/2004 | van Dongen et al. ........... | 435/6 |
| 2002/0192692 A1 * | 12/2002 | Palanisamy et al. ........... | 435/6 |
| 2003/0096255 A1 * | 5/2003 | Felix et al. ..................... | 435/6 |

FOREIGN PATENT DOCUMENTS

| | | |
|---|---|---|
| WO | WO 96/04000 | 2/1996 |
| WO | WO 97/14026 | 4/1997 |
| WO | WO 98/51817 | 11/1998 |
| WO | WO 02/093130 | 11/2002 |

OTHER PUBLICATIONS

Sinclair et al., Improved sensitivity of BCR-ABL detection : A triple - probe three-color fluorescence in situ hybridization system. Blood 90(4) : 1395-1402 (1997).*
US 5,714,331 (withdrawn).
U.S. Appl. No. 11/121,086, Poulsen.
Speel, *Histochem. Cell Biol.*, 112: 89-113 (1999).
Rudkin and Stollar, *Nature*, 265: 472-73 (1977).
Luke and Shepelsky, *Cell Vision* 5: 49-53 (1998).
Szeles, *Acta Microbiol., Immunol. Hungarica*, 49: 69-80 (2002).
Eils et al., *Cytogenetics Cell Genet.* 82: 160-71 (1998).
Macville M. et al., *Histochem. Cell. Biol.* 108: 299-305 (1997).
Tkachuk et al., *Science* 250: 559-62 (1990).
Henegariu et al., *Lab. Invest.*, 81: 483-91 (2001).
Schrock et al., *Science*, 273: 494-497 (1996).
Fan et al., *Genetic Testing*, 4: 9-14 (2000).
Hilgenfeld et al., *British J. Haematol.* 113: 305-17 (2001).
Liehr et al., *Cytogenet. Genome Res.* 97: 43-50 (2002).
Anderson et al., *Radiation Research* 159, 40-48 (2003).
Nederlof et al., *Cytometry* 11: 126-131 (1990).
Dauwerse et al., *Human Molecular Genetics*, vol. 1, No. 8 593-598.
Pellestor et al., *Chromosome Research* 10: 359-367, (2002).
S. Strehl et al., "The network of fusion genes," *Blood* 102: 845a-846a Abstract (2003).
M. Van Der Burg et al., "Split-signal FISH for detection of chromosome aberrations in acute lymphoblastic leukemia," *Leukemia*, 18 (5): 895-908 (2004).
M. Van Der Burg et al., "Rapid and sensitive detection of all types of MLL gene translocations with a single FISH probe set," *Leukemia*, 13 (12): 2107-2113 (1999).
K. A. Rack et al., "FISH detection of chromosome 14q32/lgH translocations: Evaluation in follicular lymphoma," *British J. Haematol.*, 103 (2): 495-504 (1998).
Z. Chen et al., "Some Observations on Fluorescence in Situ hybridization Evaluation of Chronic Myelocytic Leukemia," *Cancer Genetics and Cytogenetics* 98 (1): 1-3 (1997).
M. Koenig et al., "A highly specific and sensitive fluorescence in situ hybridization assay for the detection of t (4;11)(q21;q23) and concurrent submicroscopic deletions in acute leukaemias," *British J. Haematol.*, 116 (4): 758-764 (2002).

* cited by examiner

*Primary Examiner*—Ethan Whisenant
(74) *Attorney, Agent, or Firm*—Finnegan, Henderson et al.

(57) ABSTRACT

The present invention relates to methods for detecting a change in chromosomal structure. These methods employ labeled probes that bind nucleic acids. For example, these probes may be comprised of nucleic acids or nucleic acid analogs and a detectable label.

24 Claims, 10 Drawing Sheets

METHODS FOR DETECTING CHROMOSOME ABERRATIONS

This application claims priority to U.S. Provisional Patent Application Nos. 60/567,440, and 60/567,570, both of which were filed May 4, 2004, and which are both incorporated herein by reference in their entirety.

The present invention, in one embodiment, relates to methods for detecting a change in chromosomal structure. These methods employ probes that bind nucleic acids. For example, these probes may be comprised of nucleic acids or nucleic acid analogs and a detectable label.

Detection of nucleic acid sequences by in situ hybridization, involving fundamental processes in molecular biology, using non-radioactive labels, has been applied for several years (Speel, *Histochem. Cell Biol.*, 112:89-113 (1999)). Probe-based assays are useful in the detection, identification, quantitation or analysis of nucleic acids. Nucleic acid probes have long been used to analyze samples for the presence of nucleic acid from bacteria, fungi, virus or other organisms and are also useful in examining genetically-based disease states or clinical conditions of interest.

Fluorescence in-situ hybridization (FISH) was initially developed in the late 1970s (Rudkin and Stollar, *Nature*, 265:472-73 (1977)). The technique generally entails preparing a sample, labeling probes, denaturing target chromosomes and the probe, hybridizing the probe to the target sequence, and detecting a signal. Since its inception, FISH has become an important tool for determining the number, size or location of specific DNA sequences in mammalian cells. In these cells, chromosomes are arranged in pairs, where each chromosome in a pair is a sister chromosome. For example, human cells have 23 pairs of chromosomes. Typically, the hybridization reaction fluorescently stains the target sequences so that their location, size or number can be determined using fluorescence microscopy, flow cytometry or other suitable instrumentation. DNA sequences ranging from whole genomes down to several kilobases can be studied using current hybridization techniques in combination with commercially available instrumentation.

FISH-based staining is sufficiently distinct such that the hybridization signals can be seen both in metaphase spreads and in interphase nuclei. Single and multicolor FISH, using probes for detection of nucleic acids, have been applied to different clinical applications generally known as molecular cytogenetics, including prenatal diagnosis, leukemia diagnosis, and tumor cytogenetics. In general, the FISH technique has several advantages including ease of use, rapid results, reduced background in comparison with the radioactive labels that preceded fluorescent labels, and high sensitivity.

The FISH technique has several applications in the clinical setting. These applications include, for example, detection of chromosomal aneuploidy in prenatal diagnoses, hematological cancers, and solid tumors; detection of gene abnormalities such as gene amplifications, gene deletions, or gene fusions; chromosomal structural abnormalities such as translocations, duplications, insertions, or inversions; detection of contiguous gene syndromes such as microdeletion syndrome; monitoring the genetic effect of therapy; detection of viral nucleic acids in somatic cells and viral integration sites in chromosomes; gene mapping; and cell cycle analysis (Luke and Shepelsky, Cell *Vision* 5:49-53 (1998)).

With regard to applications in cancer research, FISH analysis has lead to the identification of several deletion-prone regions in human chromosomes that have been correlated with cancers in various tissues including breast, kidney, lung, uterus, testis, and ovaries (Szeles, *Acta Microbiol. Immunol. Hungarica,* 49:69-80 (2002)). FISH analysis has also been used to analyze tumor-suppressor genes and DNA repair genes. Furthermore, FISH has also been used in detecting cancers associated with translocations, such as lymphomas.

There are several variations of the FISH technique those in the art have used to analyze chromosomes (Luke and Shepelsky, *Cell Vision* 5:49-53 (1998)). For example, in comparative genomic hybridization (CGH) whole genomes are stained and compared to normal reference genomes for the detection of regions with aberrant copy number. In the multicolor-FISH technique (m-FISH or multiplex FISH) each separate normal chromosome is stained by a separate color (Eils et al, *Cytogenetics Cell Genet* 82:160-71 (1998)). When used on abnormal material, the probes will stain the aberrant chromosomes thereby deducing the normal chromosomes from which they are derived (Macville M et al., *Histochem Cell Biol.* 108: 299-305 (1997)). Specific DNA sequences, such as the ABL gene, can be reliably stained using probes of only 15 kb (Tkachuk et al., *Science* 250: 559-62 (1990)). In telomeric multiplex FISH (TM-FISH), there is a simultaneous hybridization of several subtelomeric probes on one sample slide (Henegariu et al., *Lab. Invest.,* 81:483-91 (2001)). These subtelomeric probes are between 100 kb and 1 Mb from the end of the chromosomes.

Spectral karyotyping (SKY) uses charge coupled device (CCD) imaging and Fourier spectroscopy to assess the spectrum of fluorescent wavelengths for each pixel scanned, assigning a specific pseudocolor depending on the spectrum identified (Schrock et al., *Science,* 273:494-497 (1996)). In cases of chromosomal aberrations involving small genomic segments, SKY analysis may require supplemental FISH analysis using smaller subtelomeric probes (Fan et al., *Genetic Testing,* 4:9-14 (2000); Hilgenfeld et al., *British J. Haematol.,* 113:305-17 (2001)).

Figure 1:
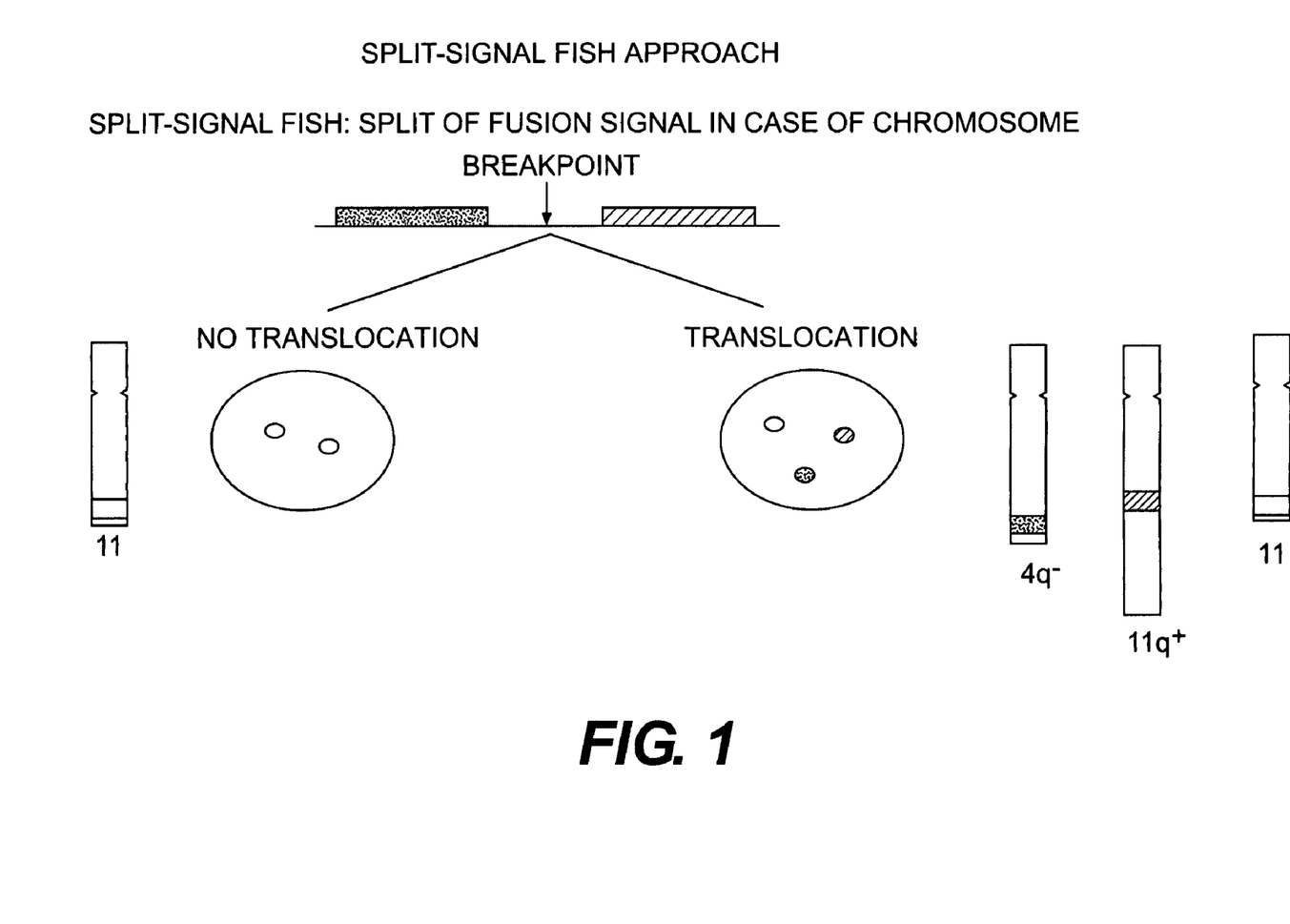
FIG. 1 summarizes the expected signals in the ssFISH method. Unshaded bars and circles represent a fused signal while the two different shaded bars and circles represent the individual signals of two different colored probes.

Split-signal FISH (ssFISH) detects changes in chromosomal structure by using two probes, each of which is labeled by a different detectable label. The detectable labels should be distinguishable from one another. Each probe binds to the chromosome on either side of a suspected breakpoint in the chromosome. In a normal chromosome, the two probes will be proximal enough to each other such that the combined signal of their different labels forms a signal that is different from each label alone. Thus, a normal chromosomal sample will contain only the combined or fused signal of the two probes on the sister chromosomes. In an abnormal sample, where one sister chromosome has broken at the suspected break point, the fused signal will remain on the normal sister chromosome. On the broken chromosome, one probe migrates to a different chromosome, where the individual signal of that probe becomes apparent. The other individual probe remains on the split chromosome and, because it is no longer proximal to the other probe, emits it's individual signal as well. In sum, because of the break in chromosomal structure, the two probes are no longer juxtaposed, allowing the fused signal they cause together to split into the individual signals for each probe. See FIG. 1. See generally WO 98/51817.

A caveat of ssFISH, however, lies in the fact that a false negative reading can emerge. Specifically, the chromosomal translocation may occur and the probe signal may actually be split between two different pairs of chromosomes, but the abnormal sample appears as though only fused signals are present. This happens when the two chromosome pairs involved in the translocation physically overlap each other spatially in the sample, bringing the split probes in proximity to give a false fused signal.

Figure 2:
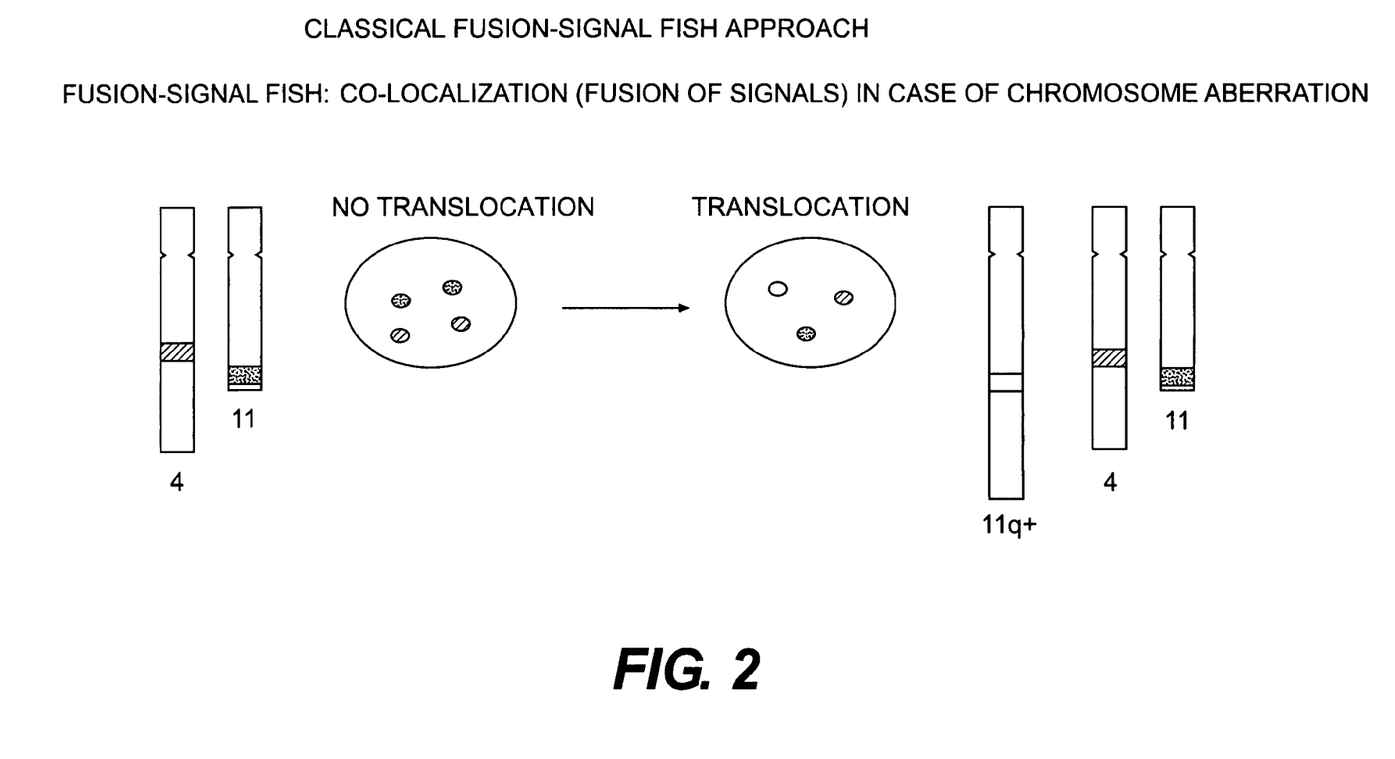
FIG. 2 summarizes the expected signals in the fusion-signal FISH method. Unshaded bars and circles represent a fused signal while the two different shaded bars and circles represent the individual signals of the two different colored probes.

Fusion-signal FISH is similar to ssFISH in that two probes with two different, distinguishable labels are used such that proximity of the two labels produces a new fused signal. The two methods differ in that for fusion-signal FISH, the two probes bind to two different chromosomal pairs at locations that are suspected to become proximal to each other as a result of a chromosomal rearrangement. Thus, in a normal sample, only signals from the individual probes are present and no fused signal appears. In an abnormal sample, where a piece of one chromosome has attached to another chromosome, the normal chromosomes in each of the two pairs involved will still emit each of the individual probe signals. In the abnormal chromosome, in which the probes are now proximal due to the translocation, the fused signal appears. See FIG. 2.

The fusion-signal FISH method can give a false positive reading. Specifically, a normal chromosomal sample could falsely give a positive fused signal even though the two probes still separately bind to different chromosomal pairs. In this case, the two chromosome pairs involved in the translocation physically overlap each other spatially in the sample, bringing the normally split probes in proximity to give a false fused signal. As discussed below, the present invention employs a new method that overcomes the problem of false positive and false negative readings.

Methods based on in situ hybridization of probes to a target nucleic acid sequence are also fraught with problems of high background due to large probes binding to non-target sequences. For example, a large component of the human genome comprises non-target repeat sequences. Heat denaturation and reannealing studies on DNA of higher organisms have distinguished three populations of eukaryotic DNA; a quickly reannealing component representing 25% of total DNA, an intermediate component that represents 30% of the total DNA, and a slow component that represents 45% of the total DNA (Britten et al., *Science* 161: 529-540 (1968)). Sequence analysis has shown that the slow component is made up of single-copy sequences, which include protein encoding genes, while the fast and intermediate components represent repetitive sequences. The fast component contains small (a few nucleotides long), highly repetitive DNA sequences, which are usually found in tandem while the intermediate component contains the interspersed repetitive DNA (Novick et al., *Human Genome Bioscience*, 46(1): 32-41 (1996) and Brosius J., *Science* 251: 753 (1991)). The repetitive units of the intermediate component are interspersed within the genome and is the major reason that large genomic nucleic acid probes (i.e. >100 bp) derived from genomic nucleic acid may not be well suited for hybridization analysis.

Interspersed repeated sequences are classified as either SINEs (short interspersed repeated sequences) or LINEs (long interspersed repeated sequences) (Kroenberg et al., *Cell*, 53: 391-400 (1988)). In primates, each of these classes are dominated by a single DNA sequence family, both of which are classified as retrosponos (Rogers J., *Internat. Rev. Cytology*, 93: 187-279 (1985)). The major human SINEs are the Alu-repeat DNA sequence family. The Alu-repeat DNA family members are characterized by a consensus sequence of approximately 280 to 300 bp which consist of two similar sequences arranged as a head to tail dimer. Approximately one million copies of the Alu repeat sequence are estimated to be present per haploid human genome, thereby representing about ten percent of the genome (Ausubel et al., *Current Prot. Mol. Bio.*, John Wiley & Sons, Inc., 1996)). That estimate is consistent with the recent sequence determination of the human chromosome 21 and 22. These reports demonstrate that Alu repeats cover 9.48% and 16.80% of the DNA, respectively (Hattori et al. *Nature*, 405: 311-319 (2000) and Dunham I. et al., *Nature*, 402:489-495 (1999)).

Alu elements have amplified in the human genome through retroposition over the past 65 million years and have been organized into a wealth of overlapping subfamilies based on diagnostic mutations shared by subfamily members (See For Example: Batzer et al., *J. Mol. Evol.*, 42: 3-6 (1996)). Batzer et al. described a consensus nomenclature for Alu repeats sequences; representing the oldest (J), intermediate (S) and young (Y) family branches. Only the Y family branch is still transcriptional active but it is very small as each of the defined a5, a8 and b8 subfamily members have produced less than 2000 elements (Sherry et al., *Genetics*, 147: 1977-1982 (1997)). It has been calculated that of the primate Alu repeat family branches, approximately one-fifth belong to the J family and four-fifths to the S family (Britten, R. J., *PNAS-USA*, 91: 6148-6150 (1994). The S family is dominated by the Sx subfamily as it represents more than 50% of the total S family branch.

In addition to SINEs and LINEs, there are several other types of repeats that are known to exist in genomic nucleic acid of humans as well as in other organisms. Chromosome telomeres are repeat sequences that appear to exist only, or else predominately, at the termini of all chromosomes. They are believed to shorten during the life of an organism and may play a role in the aging of an organism (See: Landsorp, P., WIPO Patent Application No. WO97/14026). Likewise, chromosome centromeres contain distinct repeat sequences that exist only, or else predominately, in the central (centromere) region of a chromosome. Certain of the centromere repeat sequences can be detected in all chromosomes of an organism whilst other repeat sequences are unique to a particular chromosome and can be used to identify specific chromosomes (Taneja et al., *Genes, Chromosomes & Cancer*, 30: 57-63 (2001)).

Telomere and centromere repeat sequences differ from interspersed repetitive sequence, such as SINE and LINEs, in that the telomere and centromere repeat sequences are localized within a certain region of the chromosome. By comparison, SINEs and LINEs, which are referred to herein as randomly distributed repeat sequences, are dispersed randomly throughout the entire genome (Ullu E., *TIBS:* 216-219 (June, 1982)). Thus, as used herein, the term "randomly distribute repeat sequence" is intended to refer to repeat sequences that occur randomly within all, or essentially all, genomic nucleic acids of an organism. These include, but are not limited to, Alu-repeats, Kpn-repeats, di-nucleotide repeats, tri-nucleotide repeats, tetra-nucleotide repeats, penta-nucleotide repeats, hexa-nucleotide repeats, MIR repeats, and LTR repeats, all of which are more generally classified as SINEs or LINEs.

Detection of nucleic acid sequences by in situ hybridization using non-radioactive labels has been applied for almost twenty years. As stated above however, the randomly distributed repeat sequences, such as SINEs and LINEs, are particularly problematic for the production of specific nucleic acid probes that are derived from large clones because the probes will inevitably comprise randomly distributed repeat sequence. The problem arises because the nucleic acid probes will have the randomly distributed repeat sequence contained therein, thereby facilitating hybridization between the randomly distributed repeat sequences of the probes and natural genomic nucleic acid found within all chromosomes. Because the detectable probes hybridize specifically to the target, as well as to repeat sequences randomly found in the genomic nucleic acid, a high degree of background signal results.

Thus, in one embodiment, the present invention minimizes non-specific background signal noise.

SUMMARY OF THE INVENTION

Figure 3:
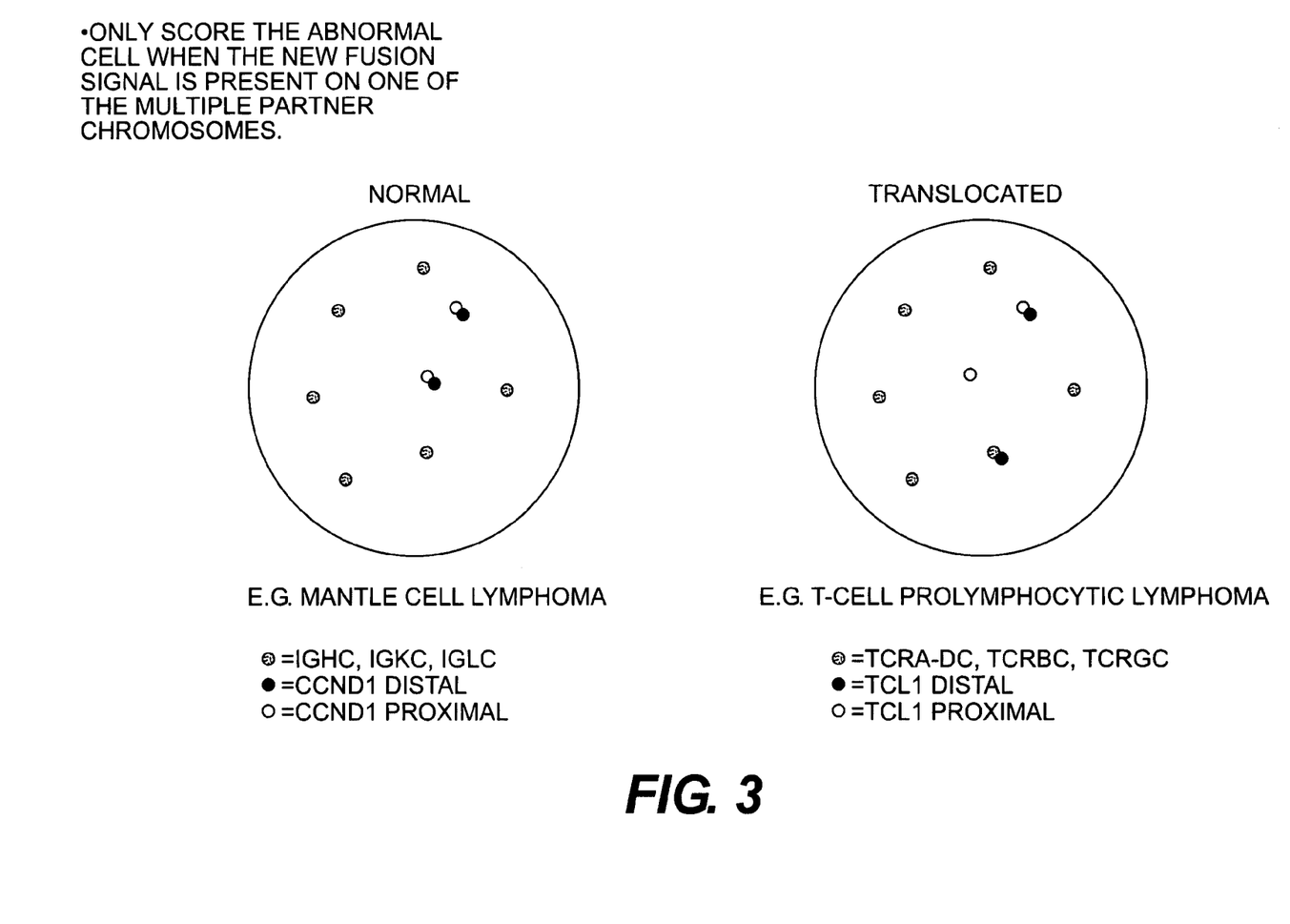

In one embodiment, herein referred to as Split-Fusion FISH (SF-FISH), at least three different probes with at least three different, distinguishable labels are used. In one embodiment, two of the probes bind to a target area in a preparation of nucleic acid. A preparation of nucleic acids includes, but is not limited to, a preparation of chromosomes, BACs, YACs, plasmids, and cosmids. In another embodiment, the target areas may be on either side of a suspected breakpoint in a chromosome such that the two probes are proximal enough to yield a first fused signal. The third probe binds to a different target area in the sample and manifests its own independent signal. For example, this may include binding to one chromosome, a specific group of chromosomes, or all of the other chromosomes in the sample except for those bound by the other two probes. When a change in nucleic acid structure occurs, the first fused signal splits into its respective individual signals due to the loss of proximity of the first two probes. In addition, a new fused signal appears due to a new proximity of the third probe to one of the two other probes. A change in nucleic acid structure is positively identified when the first fused signal is lost, a new split signal emerges, and a new second fused signal appears. See FIG. 3. In another embodiment, at least one of the at least three probes used in the SF-FISH method is pre-absorbed with complementary repetitive non-target sequences, removing labeled probe that may bind to repetitive non-target sequences in the sample before use in the SF-FISH method.

In another embodiment, the complementary repetitive non-target sequences are attached to a solid surface. For example, beads may be used. See FIG. 4.

Additional objects and advantages of the invention will be set forth in part in the description which follows or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed. The accompanying drawings, which are incorporated in and constitute a part of this specification, illustrate embodiments of the invention and together with the description, serve to explain the principles of the invention.

BRIEF DESCRIPTION OF THE DRAWINGS

FIG. 3 summarizes the expected signal combinations resulting from a SF-FISH method. Unshaded and lightly shaded circles shown together represent the first fused signal resulting from the proximity of two of the three probes, which have different colors such as red and green. Darkly shaded circles represent the third probe. The darkly shaded and lightly shaded circles together represent the new fused signal while the unshaded circle alone represents the new split signal resulting from a change in chromosomal structure. In one embodiment, the IGHC, IGKC, and IGLC probes, represented here by the darkly shaded circles, are marked with a third, fourth, and fifth label, each label generating a unique fused signal with the differently colored lightly shaded label, thereby identifying the fusion partner.

FIG. 5 summarizes how unlabeled blocking DNA may be used to avoid unwanted signals. In this figure, two "red probes" are depicted at the top left using thin lines, four "green probes" are depicted at the top right using heavy lines. The "blocking probe" is depicted using medium-weight lines. The "red probes" are lightly shaded in the bars and circles below, while the "green probes" are darkly shaded. The fused signals are unshaded.

FIG. 6 shows hybridization of BCR probes to metaphase chromosomes. (A) Drawing of the area covered by the probes, with different colored probes denoted by short and long dashed lines; (B) Hybridization of the BCR probes to metaphase spreads from normal peripheral blood. Two normal BCR loci on chromosomes 22 are represented by two dots or co-localized signals from two differently colored probes (e.g. yellow, or juxtaposed green and red signals); (C) Hybridization of the BCR probes to nuclei from normal peripheral blood. Two normal BCR loci are represented by two light colored dots or co-locolized signals from two differently colored probes; (D) Hybridization of the BCR probes to metaphase spreads from the cell line BV173. One normal BCR locus on chromosome 22 is represented by a light colored dot or co-locolized signals from two differently colored probes (see the bright dots at the top left of the figure). Two derivative chromosomes resulting from a translocation between chromosome 9 and 22 (in cell line BV173) can be detected. An additional chromosome 9 can be detected as a result of an amplification of the derivative chromosome 9; (E) Hybridization of the BCR probes to nuclei from the cell line BV173. One normal BCR locus is represented by a light colored dot or co-locolized signals from two different colored probes. (See the brightly colored dots at the top right side of the nuclei pictured here.) Two derivative chromosomes resulting from a translocation between chromosome 9 and 22 (in cell line BV173) can be detected. An additional chromosome 9 can be detected as a result of an amplification of the derivative chromosome 9.

FIG. 7 shows hybridization of ETV6 probes to metaphase chromosomes. (A) Drawing of the area cover by the probes, with different colored probes denoted by short and long dashed lines; (B) Hybridization of the ETV6 probes to metaphase spreads from normal peripheral blood. Two normal ETV6 loci on chromosomes 12 are represented by two light colored dots or co-locolized different color signals; (C) Hybridization of the ETV6 probes to nuclei from normal peripheral blood. Two normal ETV6 loci are represented by two light colored dots or co-locolized different colored signals; (D) Hybridization of the ETV6 probes to metaphase spreads from the cell line REH. The normal ETV6 locus on chromosome 12 is deleted, represented by the lack of a light colored dot or co-localized different colored signals. Instead, each signal shown on this spread is one pure color (green or red). Two derivative chromosomes resulting from a translocation between chromosome 12 and 21 (in cell line REH) can be detected. A small green signal can be detected as a remaining part of the deleted ETV6 locus; (E) Hybridization of the ETV6 probes to nuclei from the cell line REH. The normal ETV6 locus on chromosome 12 is deleted, represented by the lack of a light colored dot or co-localized different color signals. Two derivative chromosomes resulting from a translocation between chromosome 12 and 21 (in cell line REH) can be detected. A small green signal can be detected as a remaining part of the deleted ETV6 locus (top right and bottom left dots on this spread).

FIG. 8 shows hybridization of MLL probes to metaphase chromosomes. (A) Drawing of the area cover by the probes, with different colored probes denoted by short and long dashed lines; (B) Hybridization of the MLL probes to metaphase spreads from normal peripheral blood. Two normal MLL loci on chromosomes 11 are represented by two light colored dots or co-localized different colored signals (all four dots shown); (C) Hybridization of the MLL probes to nuclei from normal peripheral blood. Two normal MLL loci are represented by two light colored dots or co-localized different colored signals (all dots shown); (D) Hybridization of the MLL probes to metaphase spreads from the cell line RS-4; 11. One normal MLL locus on chromosome 11 is represented by a light colored dot or co-localized different colored signals (at top right). Two derivative chromosomes resulting from a translocation between chromosome 4 and 11 (in cell line RS-4; 11) can be detected; (E) Hybridization of the MLL probes to nuclei from the cell line RS-4; 11. One normal MLL locus on chromosome 11 is represented by a light colored dot or co-localized different colored signals (larger dots on the spread at top right and at bottom). Two derivative chromosomes resulting from a translocation between chromosome 4 and 11 (in cell line RS-4; 11) can be detected.

FIG. 9 shows hybridization of TCF3 probes to metaphase chromosomes. (A) Drawing of the area cover by the probes, with different colored probes denoted by short and long dashed lines; (B) Hybridization of the TCF3 probes to metaphase spreads from normal peripheral blood. Two normal TCF3 loci on chromosomes 19 are represented by two light colored dots or co-localized different colored signals; (C) Hybridization of the TCF3 probes to nuclei from normal peripheral blood. Two normal TCF3 loci are represented by two light colored dots or co-localized different colored signals; (D) Hybridization of the TCF3 probes to metaphase spreads from the cell line 697. One normal TCF3 locus on chromosome 19 is represented by a light colored dot or co-localized different colored signals (two bright dots at right). Two derivative chromosomes resulting from a translocation between chromosome 1 and 19 (in cell line 697) can be detected; (E) Hybridization of the TCF3 probes to nuclei from the cell line 697. One normal TCF3 locus on chromosome 19 is represented by a light colored dot or co-localized different colored signals (central juxtaposed dots on the spread). Two derivative chromosomes resulting from a translocation between chromosome 1 and 19 (in cell line 697) can be detected.

FIG. 10 shows hybridization of TLX3 probes to metaphase chromosomes. (A) Drawing of the area cover by the probes, with different colored probes denoted by short and long dashed lines; (B) Hybridization of the TLX3 probes to metaphase spreads from normal peripheral blood. Two normal TLX3 loci on chromosomes 5 are represented by two light colored dots or co-localized different colored signals (all dots shown here); (C) Hybridization of the TLX3 probes to nuclei from normal peripheral blood. Two normal TLX3 loci are represented by two light colored dots or co-localized different colored signals; (D) Hybridization of the TLX3 probes to metaphase spreads from the cell line HPB-ALL. One normal TLX3 locus on chromosome 5 is represented by a light colored dot or co-localized different colored signals (at top right). Two derivative chromosomes resulting from a translocation between chromosome 5 and 14 (in cell line HPB-ALL) can be detected; (E) Hybridization of the TLX3 probes to nuclei from the cell line HPB-ALL. One normal TLX3 locus on chromosome 5 is represented by a light colored dot or co-localized different colored signals (dot at center). Two derivative chromosomes resulting from a translocation between chromosome 5 and 14 (in cell line HPB-ALL) can be detected.

Color versions of FIGS. 1-10(e) are provided in Provisional Application 60567,440, to which this application claims priority and which is incorporated by reference herein.

DESCRIPTION OF THE INVENTION

In one embodiment, the present invention provides a method for detecting changes in chromosomal structure. As used herein, the phrase change in chromosomal structure refers to an alteration in the chromosomes in a test sample as compared to a normal chromosome control. As used herein, a euploidy is the condition of having a normal number of structurally normal chromosomes. For example, somatic euploid cells from a human female contain 44 autosomal chromosomes and two X-chromosomes for a total of 46 chromosomes or 23 chromosomal pairs. Euploid bulls have 58 autosomal chromosomes, one X-chromosome, and one Y-chromosome.

Non-exhaustive examples of chromosomal alterations include aneuploidy, gene amplifications, deletions including gene deletions, gene fusions, translocations, duplications, insertions, or inversions. As used herein, aneuploidy refers to any deviation from the normal euploid state or the condition of having less than or more than the normal diploid number of chromosomes. Aneuploidy is the most frequently observed type of cytogenetic abnormality. Generally, aneuploidy is recognized as a small deviation from euploidy because major deviations are rarely detected because of the lethal nature of major changes in chromosome number. As used herein, an amplification refers to an increase in the number of copies of a specific DNA fragment. Such DNA fragments include, for example, a gene or an entire chromosome. As used herein, a deletion refers to a genetic event in which a nucleic acid sequence has been removed from a chromosome. As used herein, a gene fusion refers to an accidental joining of the DNA of two genes. Gene fusions may occur by translocations or inversions. Gene fusions may give rise to hybrid proteins or the misregulation of the transcription of one gene due to the juxtaposition of cis regulatory elements (e.g., enhancers or promoters) of another gene. As used herein, a translocation refers to a genetic event in which a part of the nucleic acid sequence of one chromosome is removed from that chromosome and attached to a different chromosome. As used herein, a duplication refers to the repetition of a nucleotide sequence in a chromosome or a chromosome segment. For example, a duplication may result in the repetition of a nucleotide sequence in linear juxtaposition to the duplicated sequence. As used herein, an insertion refers to a genetic event in which a nucleic acid sequence has been introduced between two points in a chromosome. As used herein, an inversion is a genetic event in which a nucleic acid sequence's orientation in a chromosome has been reversed. As used herein, a chromosomal breakpoint refers to a location in the chromosome where the chromosome breaks into two pieces.

In one embodiment, the present invention employs at least three probes that specifically bind to target nucleic acid sequences on chromosomes. A probe, as used herein, refers to a "nucleic acid" probe or to a "nucleic acid analog" probe that binds to a structure or target of interest. As used herein, a "nucleic acid" refers to a nucleobase sequence-containing oligomer, polymer, or polymer segment, having a backbone formed solely from naturally occurring nucleotides or unmodified nucleotides. As used herein, a "nucleic acid analog" means an oligomer, polymer, or polymer segment composed of at least one modified nucleotide, or subunits derived directly from a modification of nucleotides. Non-limiting examples of naturally occurring nucleobases include: adenine, cytosine, guanine, thymine, and uracil. Non-limiting examples of modified nucleotides include: 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Other non-limiting examples of suitable nucleobases include those nucleobases illustrated in FIGS. 2(A) and 2(B) of Buchardt et al. (U.S. Pat. No. 6,357,163).

The term "nucleic acid analog" also refers to synthetic molecules that can bind to a nucleic acid. For example, a nucleic acid analog probe may be comprised of peptide nucleic acids (PNAs), locked nucleic acids (LNAs), or any derivatized form of a nucleic acid. As used herein, "peptide nucleic acid" or "PNA" means any oligomer or polymer comprising at least one or more PNA subunits (residues), including, but not limited to, any of the oligomer or polymer segments referred to or claimed as peptide nucleic acids in U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470 6,201,103, 6,228,982 and 6,357,163; all of which are herein incorporated by reference. The term PNA also applies to any oligomer or polymer segment comprising one or more subunits of those nucleic acid mimics described in the following publications: Lagriffoul et al., *Bioorganic & Medicinal Chemistry Letters*, 4: 1081-1082 (1994); Petersen et al., *Bioorganic & Medicinal Chemistry Letters*, 6: 793-796 (1996); Diderichsen et al., *Tett. Lett.* 37: 475-478 (1996); Fujii et al., *Bioorg. Med. Chem. Lett.* 7: 637-627 (1997); Jordan et al., *Bioorg. Med. Chem. Lett.* 7: 687-690 (1997); Krotz et al., *Tett. Lett.* 36: 6941-6944 (1995); Lagriffoul et al., *Bioorg. Med. Chem. Lett.* 4: 1081-1082 (1994); Diederichsen, U., *Bioorganic & Medicinal Chemistry Letters*, 7: 1743-1746 (1997); Lowe et al., *J. Chem. Soc. Perkin Trans.* 1, (1997) 1: 539-546; Lowe et al., *J. Chem. Soc. Perkin Trans.* 11: 547-554 (1997); Lowe et al., *J. Chem. Soc. Perkin Trans.* 1 1:555-560 (1997); Howarth et al., *J. Org. Chem.* 62: 5441-5450 (1997); Altmann, K-H et al., *Bioorganic & Medicinal Chemistry Letters*, 7:1119-1122 (1997); Diederichsen, U., *Bioorganic & Med. Chem. Lett.*, 8:165-168 (1998); Diederichsen et al., *Angew. Chem. Int. Ed.*, 37: 302-305 (1998); Cantin et al., *Tett. Lett.*, 38: 4211-4214 (1997); Ciapetti et al., *Tetrahedron*, 53: 1167-1176 (1997); Lagriffoule et al., *Chem. Eur. J.*, 3: 912-919 (1997); Kumar et al., *Organic Letters* 3(9):1269-1272 (2001); and the Peptide-Based Nucleic Acid Mimics (PE-NAMs) of Shah et al. as disclosed in WO96/04000. As used herein, the term "locked nucleic acid" or "LNA" means an oligomer or polymer comprising at least one or more LNA subunits. As used herein, the term "LNA subunit" means a ribonucleotide containing a methylene bridge that connects the 2'-oxygen of the ribose with the 4'-carbon. See generally, Kurreck, *Eur. J. Biochem.*, 270:1628-44 (2003).

A probe may contain one or more nucleic acid segments or synthetic molecule segments, wherein each segment is separately labeled with a detectable label. A probe may also contain a mixture of nucleic acid segments and synthetic molecule segments, wherein each segment is separately labeled with a detectable label.

As used herein, a target sequence is a nucleic acid sequence sought to be detected or identified. The nucleic acid sequence can be a subsequence of a nucleic acid molecule of interest (e.g. a chromosome). As used herein, a non-target sequence is a nucleic acid sequence which is not a target sequence.

A probe binds to a target sequence under certain conditions. The term "bind" is synonymous with "hybridize." When two molecules hybridize, they form a combination of the two molecules through one or more types of chemical bonds or through complementary base pairing. In addition, bases in a probe may be joined by a linkage other than a phosphodiester bond, so long as it does not prevent hybridization. Thus, oligonucleotide probes may have constituent bases joined by peptide bonds rather than phosphodiester linkages. Appropriate hybridization conditions can be selected by those skilled in the art with minimal experimentation as exemplified in Ausubel et al. (1995), Current Protocols in Molecular Biology, John Wiley & Sons, sections 2, 4, and 6. Additionally, stringency conditions are described in Sambrook et al. (1989) Molecular Cloning: A Laboratory Manual, 2nd ed., Cold Spring Harbor Press, chapters 7, 9, and 11. As used herein, the term complementary refers to nucleobases that may hybridize to each other. For example, adenine is complementary to thymine and cytosine is complementary to guanine.

As used herein, the phrase binds under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85-90% identical, remain bound to each other.

In one embodiment, the probes comprise a detectable label. As used herein, a detectable label refers to moieties that can be attached to an oligomer or polymer to thereby render the oligomer or polymer detectable by an instrument or method. In one embodiment, a detectable label may be directly attached to a probe. In another embodiment, a detectable label may be indirectly attached to a probe. For example, a detectable label may be attached to a probe by using a linker. A detectable label may be, for example, a fluorochrome, a chromophore, a spin label, a radioisotope, an enzyme, a hapten, Quantum Dot, beads, aminohexyl, pyrene, and a chemiluminescence compound, such as acridinione. Fluorochromes that may be used in the method of the present invention include, but are not limited to, IR dyes, Dyomics dyes, phycoerythrine, cascade blue, Oregon green 488, pacific blue, rhodamine green, 5(6)-carboxyfluorescein, cyanine dyes (i.e., Cy2, Cy3, Cy 3.5, Cy5, Cy5.5, Cy 7) (diethyl-amino)coumarin, fluorescein (i.e., FITC), tetramethylrhodamine, lissamine, Texas Red, AMCA, TRITC, and Alexa dyes. Haptens that may be used in the present invention include, but are not limited to, 5(6)-carboxyfluorescein, 2,4-dinitrophenyl, digoxigenin, rhodamine, bromodeoxy uridine, acetylaminoflurene, mercury trinitrophenol, estradiol, and biotin. Enzymes that may be used in the present invention include, but are not limited to, soybean peroxidase, alkaline phosphatase, and horseradish peroxidase.

In one embodiment of the invention, the labels used are detectable and distinguishable from one another. Distinguishable probes are probes that, when detected in isolation from one another, give different signals. As used herein, fused signals result when two or more individual signals co-localize to produce a new or different signal. For example, when two labeled probes are in close enough proximity for their signals to overlap, a fused signal results. A fused signal does not require the labeled probes to bind to target sequences that are connected. A fused signal results when the labeled probes are close enough to give a co-localized signal. For example, if the difference between the probes is less than two times the diameter of the probe signal, a fused signal results. A fused signal may also result when three labeled probes are in proximity to each other, which may result due to a chromosomal insertion. These insertions occur in approximately 20% of human patients tested. A split signal thereby results when the individual signals that make up a fused signal are separated from one another such that the individual signals are separately identifiable. Labels may be detected by a variety of means including fluorescent microscopes, brightfield microscopes, cooled charge-coupled device (CCD) cameras, and digital imaging microscopy, laser scanning, flow cytometry. Probes and labeled probes may be prepared by any methods known in the art.

In one embodiment, the probes are contacted with a preparation of chromosomes. In another embodiment, the probes are contacted with a preparation of chromosomes in succession. In another embodiment, the probes are contacted with a preparation of chromosomes simultaneously. As used herein, a preparation of chromosomes refers to a composition comprised of chromosomes from a cell type of interest. A cell type of interest may be a mammalian cell, a bacterial cell, or a yeast cell. In a further embodiment, chromosome preparations may be produced from mammalian cells in various stages of mitosis. For example, chromosomal preparations may be produced from cells in interphase, prophase, anaphase, telophase, or metaphase. Methods for producing a chromosomal preparation for use in SF-FISH analysis are well known to those of skill in the art.

Figure 4:
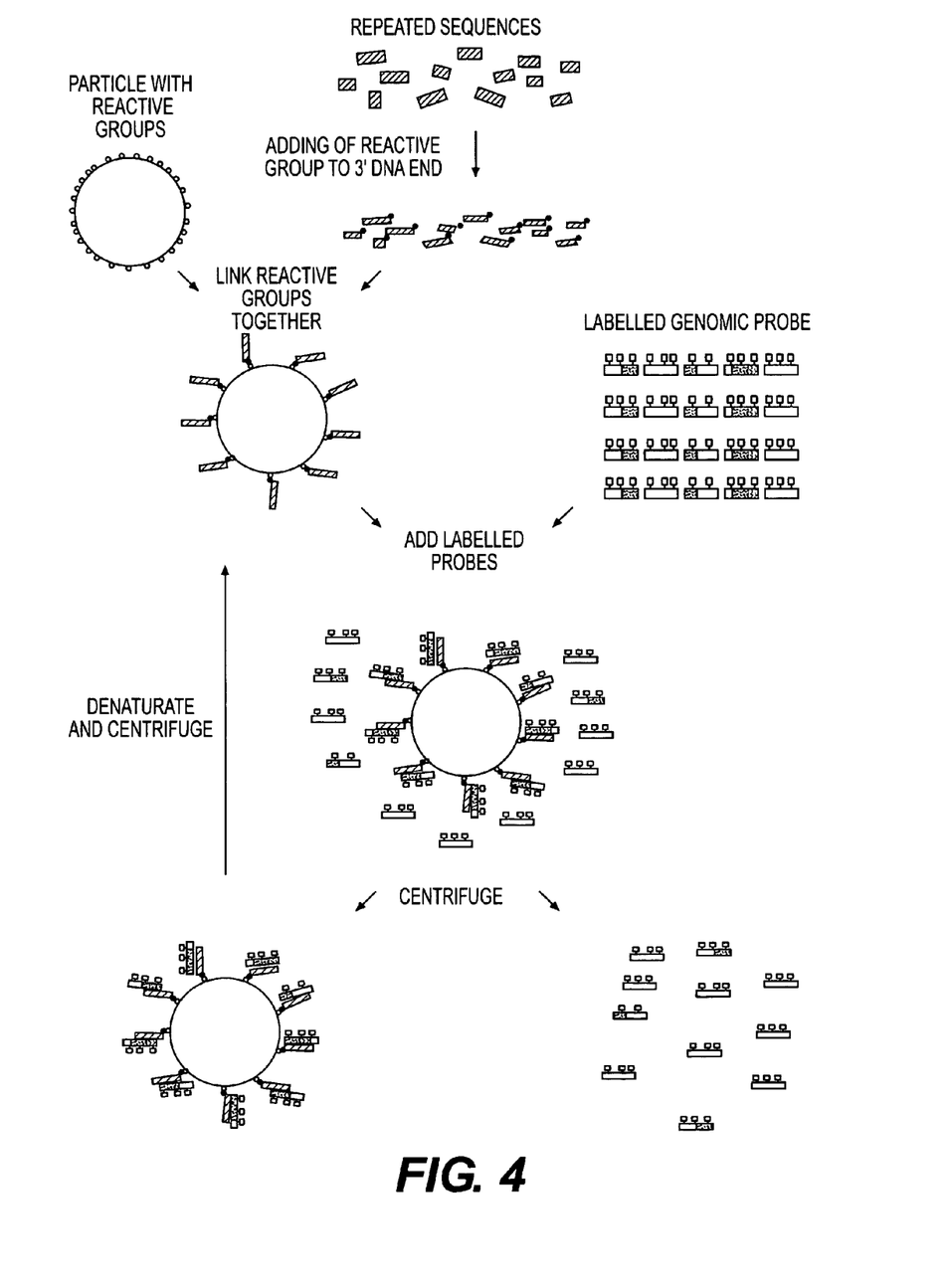
FIG. 4 summarizes how labeled probes may be pre-absorbed with repeat sequences prior to use in the present invention.

In one embodiment, the present invention minimizes non-specific background signal noise. In one example, repeat sequences may be depleted from a probe as illustrated in FIG. 4. In another example, the probe may first be hybridized to a pool of repeated nucleic acid sequences that are labeled with an antigen. The repeat sequences are then removed by contacting the sample with a surface bound antibody that recognizes the antigen, thereby using the antibody to capture probe that may bind to repeat sequences. The probe sample may then be removed from the immobilized antibodies before use in a FISH technique such as SF-FISH.

In another embodiment, the present invention minimizes the hybridization of labeled probes to a target area where the labeled probes partially or fully extend over the chromosomal breakpoint region or any other area where hybridization is not desired. Blocking may be achieved by adding excess unlabeled DNA containing a sequence that hybridizes to a region on a chromosome where labeled probe hybridization is unwanted. See FIG. 5. A blocking DNA may be prepared from various vectors including, but not limited to, a plasmid, a cosmid, a PAC, a BAC, or a YAC.

In another embodiment, one or more of the three probes used is pre-absorbed with complementary repeated nucleic acid sequences. Repeated nucleic acid sequences include, but are not limited to, Alu-repeats, Kpn-repeats, di-nucleotide repeats, tri-nucleotide repeats, tetra-nucleotide repeats, penta-nucleotide repeats, hexa-nucleotide repeats, MLR, and LTR, all of which are more generally classified as SINEs or LINEs. Repeat sequences are usually non-target sequences. As used herein, pre-absorbed refers to exposing a labeled probe to complementary repeated nucleic acid sequences to form a bound labeled probe. The bound labeled probe, bound by complementary nucleic acid sequences, is removed before using the remaining labeled probe in the SF-FISH method. In yet another embodiment, the complementary repeated nucleic acid sequences are linked to a solid surface. Solid surfaces include, but are not limited to, beads and slides. In one embodiment, repeated sequences may be covalently linked to a solid surface. In another embodiment, repeated sequences may be hydrogen bonded to a solid surface.

The present invention includes a method for detecting a change in chromosomal structure comprising removing undesired sequences from a labeled probe. Undesired sequences include, but are not limited to, repeat nucleotide sequences.

The present invention includes a method for detecting a change in a target area comprising:
  (a) obtaining a preparation of nucleic acids;
  (b) contacting the preparation of nucleic acids with a first probe containing a first label;
  (c) contacting the preparation of nucleic acids with a second probe containing a second label, wherein the first probe and the second probe bind within the same target area in a normal control sample, and wherein the binding of the first probe and second probe results in a fused signal;
  (d) contacting the preparation of nucleic acids with a third probe containing a third label, wherein the third probe binds a different target region in the preparation of nucleic acids; and
  (e) detecting the change in nucleic acid structure,
    wherein the first probe and the second probe are not present on the same target area resulting in a split signal; and
    wherein
      (i) the first probe and the third probe; or
      (ii) the second probe and the third probe
    are present on the same target area resulting in a new fused signal.

The present invention includes a method for detecting a change in chromosomal structure comprising:
  (a) obtaining a preparation of chromosomes;
  (b) contacting the preparation of chromosomes with a first probe containing a first label;
  (c) contacting the preparation of chromosomes with a second probe containing a second label, wherein the first probe and the second probe bind the same chromosome in a normal control sample, and wherein the binding of the first probe and second probe results in a fused signal;
  (d) contacting the preparation of chromosomes with a third probe containing a third label, wherein the third probe binds other chromosomes or another region of the same chromosome in the preparation of chromosomes; and
(e) detecting the change in chromosomal structure,
   wherein the first probe and the second probe are not present on the same chromosome resulting in a split signal; and
   wherein
      (i) the first probe and the third probe; or
      (ii) the second probe and the third probe
   are present on the same chromosome resulting in a new fused signal.

The present invention also includes a method for detecting a change in chromosomal structure comprising:
(a) obtaining a preparation of chromosomes;
(b) contacting a first probe containing a first label with a complementary probe having a nucleotide sequence complementary to a non-target sequence which may be present in the chromosome sample to form a bound labeled probe;
(c) removing the bound labeled probe leaving a first selected probe;
(d) contacting the preparation of chromosomes with the first selected probe;
(e) contacting the preparation of chromosomes with a second probe containing a second label, wherein the first selected probe and the second probe bind the same chromosome in a normal control sample, and wherein the binding of the first selected probe and second probe results in a fused signal;
(f) contacting the preparation of chromosomes with a third probe containing a third label, wherein the third probe binds other chromosomes in the preparation of chromosomes except chromosomes bound by the first selected probe and the second probe; and
(g) detecting the change in chromosomal structure,
   wherein the first selected probe and the second probe are not present on the same chromosome resulting in a split signal; and
   wherein
      (i) the first selected probe and the third probe; or
      (ii) the second probe and the third probe
   are present on the same chromosome resulting in a new fused signal.

As used herein, the phrases "chosen from one or more of," "chosen from at least one of," "chosen from one or more," and "chosen from at least one" followed by a list of items such as A, B, and C, indicate that one or more of A, B, and C may be selected (e.g. only A; only B; only C; only A and B; only B and C; only A and C; or A, B, and C), and also indicate that one or more types within each A, B, or C category may be selected (e.g. only A1 and A2; only A1 and A2 and B1; only B1 and B2 and C1, etc.).

The following examples are provided for illustrative purposes only and are not intended to limit or restrict the scope of the invention.

EXAMPLES

Example 1

A slide containing metaphase spreads and interphase nuclei was pretreated in TBS (50 mmol/L Tris, 150 mmol/L NaCl, pH 7.6) with 3.7% formaldehyde for 2 minutes at room temperature, as described in Human Cytogenetics, a Practical Approach, Volume 1, $2^{nd}$ ed., D. E. Rooney and B. H. Czepulkowski editors (1992). The slide was then rinsed twice in phosphate buffered saline (PBS) for 5 minutes per wash at room temperature. After rinsing, the slide was dehydrated in a cold (4° C.) series of ethanol by incubating the slide in 70% ethanol at 4° C. for 2 minutes; incubating the slide in 85% ethanol at 4° C. for 2 minutes; and then incubating the slide in 96% ethanol at 4° C. for 2 minutes, followed by air drying.

On each target area, 10 μL of DNA Hybridization Buffer (100 ng fluorescein labelled probe, 100 ng Texas Red labelled probe, 5 μM PNA Oligo Mix, 45% formamide, 300 mM NaCl, 5 mM $NaPO_4$, 10% Dextran sulphate) was added and an 18×18 mm coverslip was applied to cover the hybridization area. The edges of the coverslip were sealed with rubber cement before denaturation at 82° C. for 5 minutes. The slide was hybridized overnight at 45° C. After hybridization, the coverslip was removed and the slide was washed for 10 minutes in a stringent wash buffer (0.2×SSC, 0.1% Triton X-100) at 65° C.

The slide was then rinsed in TBS for 1 minute before dehydrated in a cold (4° C.) series of 70%, 85% and 96% ethanol as described above. Each slide was mounted with 10 μL of anti-fade solution (Vectashield H-1000, Vector Laboratories, Inc. Burlingame) supplemented with 0.1 μg/mL 4,6-diamidino-2-phenylindole (DAPI, Sigma Chemicals) and sealed with a coverslip. The slide was analyzed using a fluorescence microscope equipped with a CCD digital camera.

FIGS. 6-10 provide results with probes that bind to the BCR, ETV6, MLL, TCF3, and TLX3 genes respectively. Specific probe sequences that may be used in this technique, for example, to assay the BCR, ETV6, MLL, TCF3, and TLX3 genes, were provided in Provisional Application No. 60/567,570, to which this application claims priority, and which is incorporated herein by reference. Additional probe sequences are provided in a corresponding United States application filed concurrently, and entitled "Nucleic Acid Probes and Nucleic Acid Analog Probes." That application is also incorporated by reference herein.

Example 2

Slides containing metaphase spreads and interphase nuclei from normal cells and test sample cells are pretreated in TBS as described above. The slides are then rinsed twice in PBS for 5 minutes per wash at room temperature. After rinsing, the slide are dehydrated in a cold (4° C.) series of 70%, 85%, and 96% ethanol as described above, followed by air drying.

Figure 5:
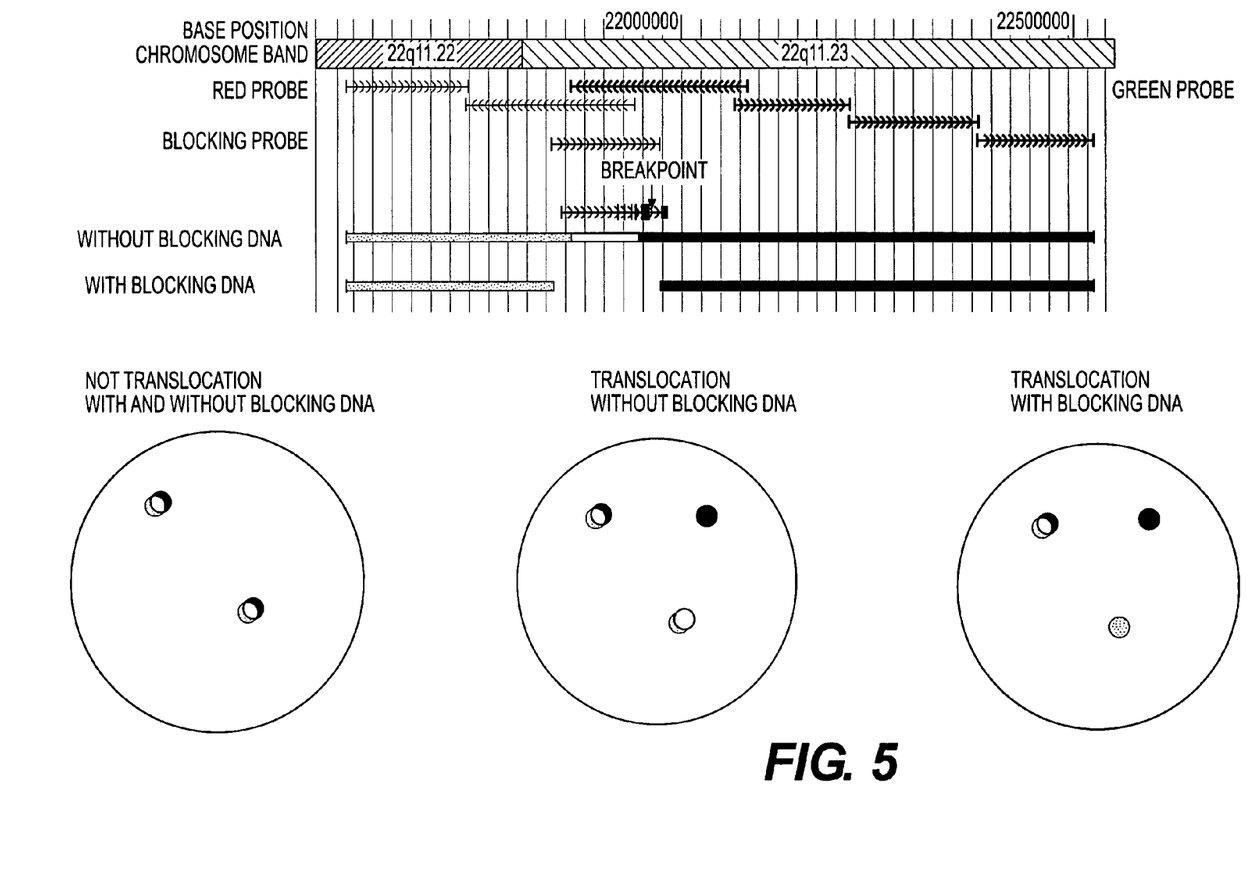
Figure 6A:
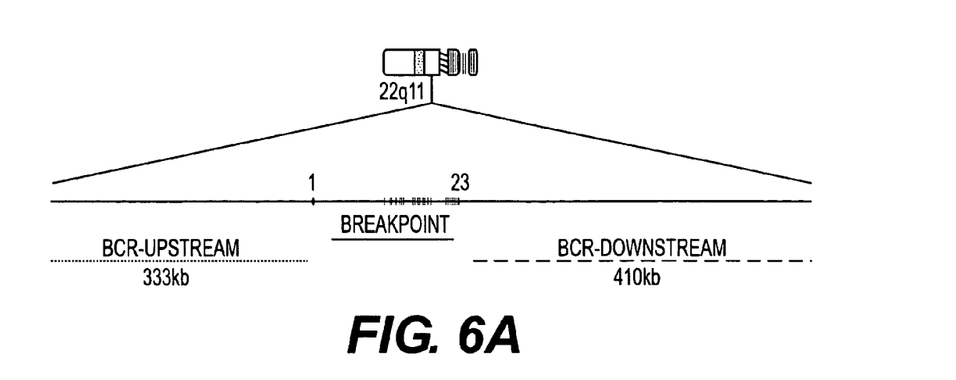
Figure 6B:
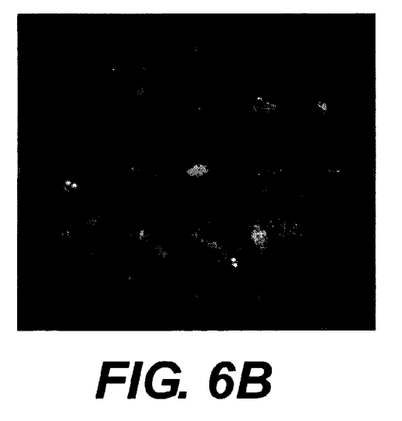
Figure 6C:
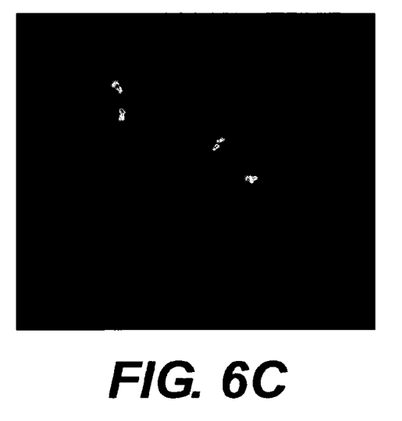
Figure 6D:
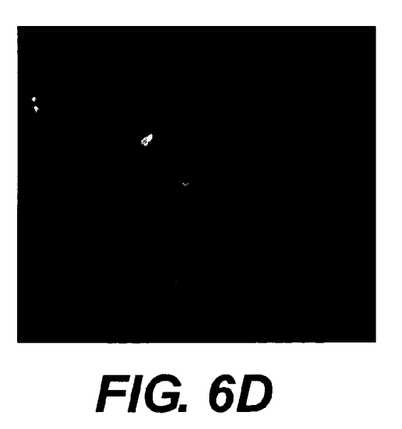
Figure 6E:
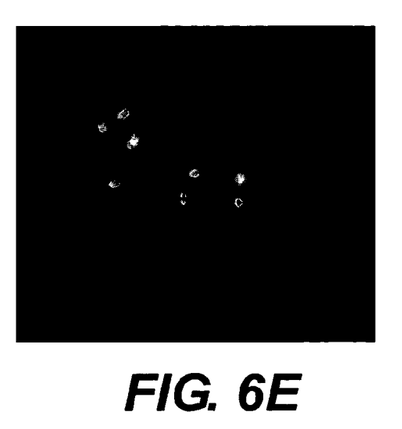
Figure 7A:
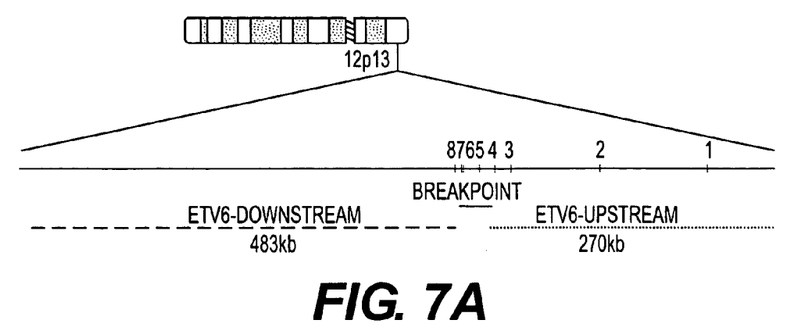
Figure 7B:
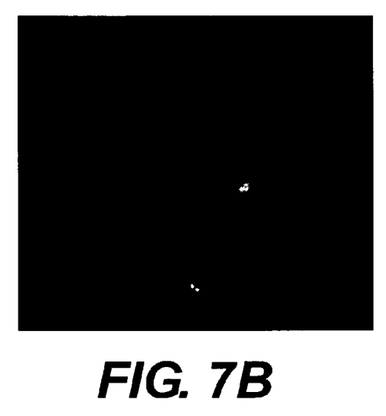
Figure 7C:
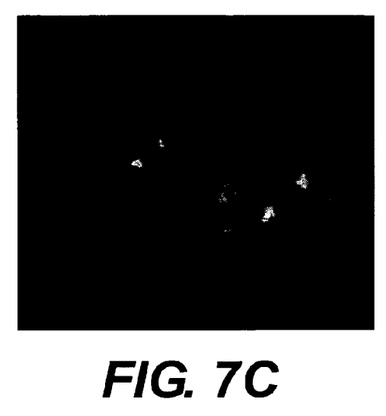
Figure 7D:
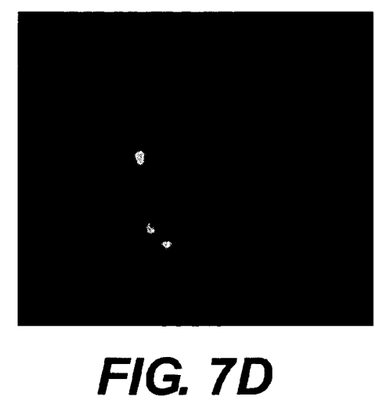
Figure 7E:
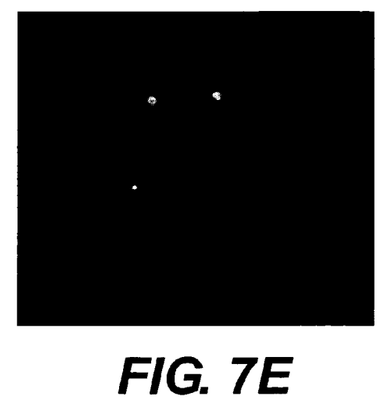
Figure 8A:
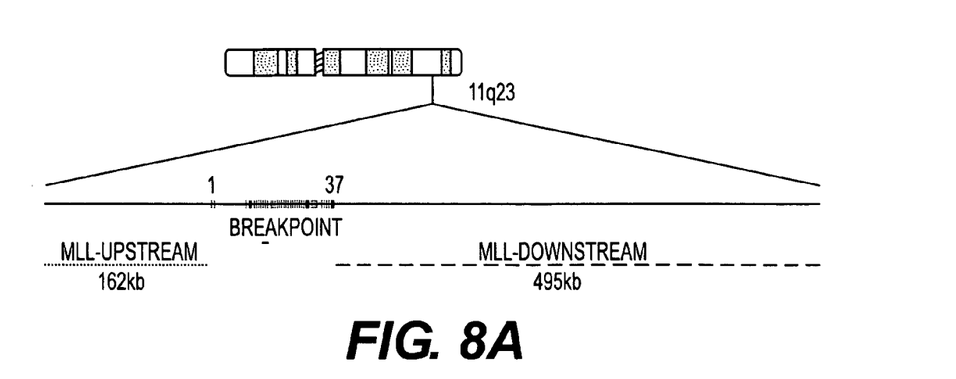
Figure 8B:
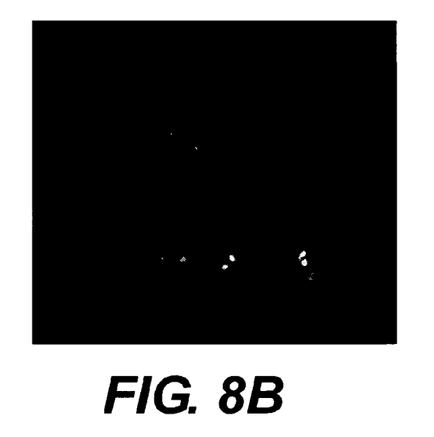
Figure 8C:
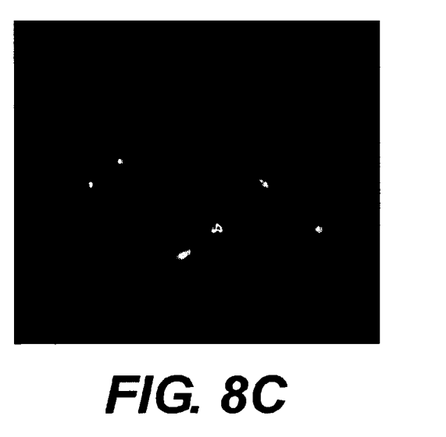
Figure 8D:
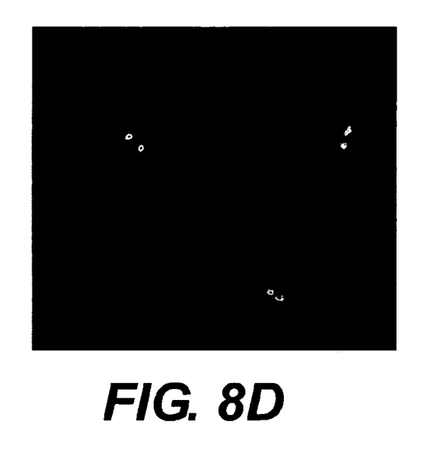
Figure 8E:
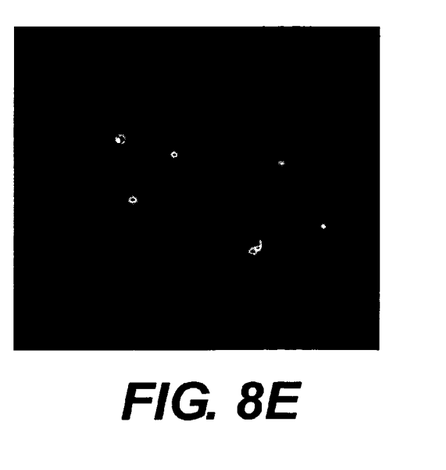
Figure 9A:
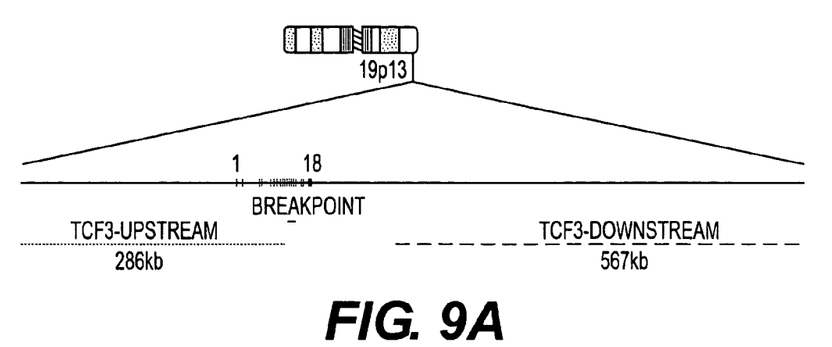
Figure 9B:
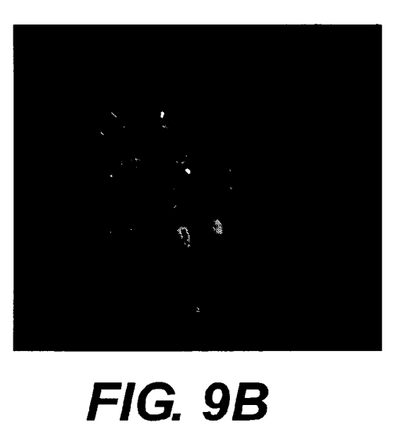
Figure 9C:
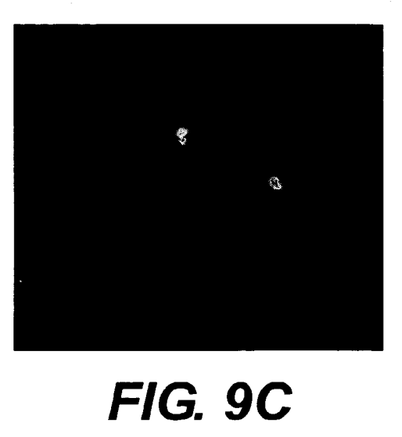
Figure 9D:
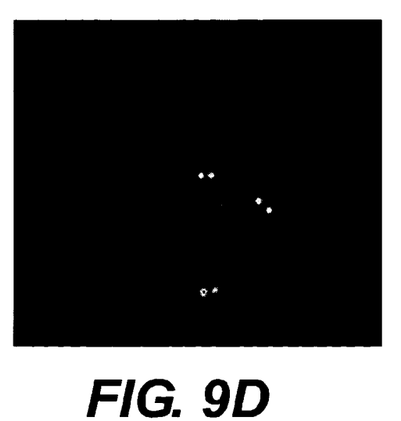
Figure 9E:
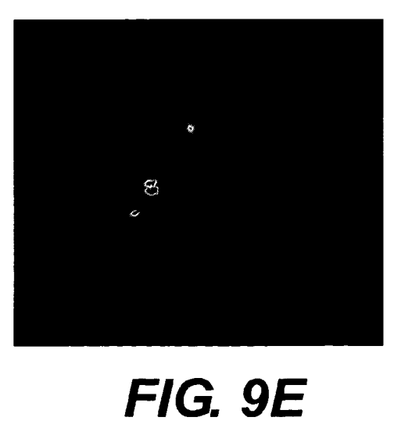
Figure 10A:
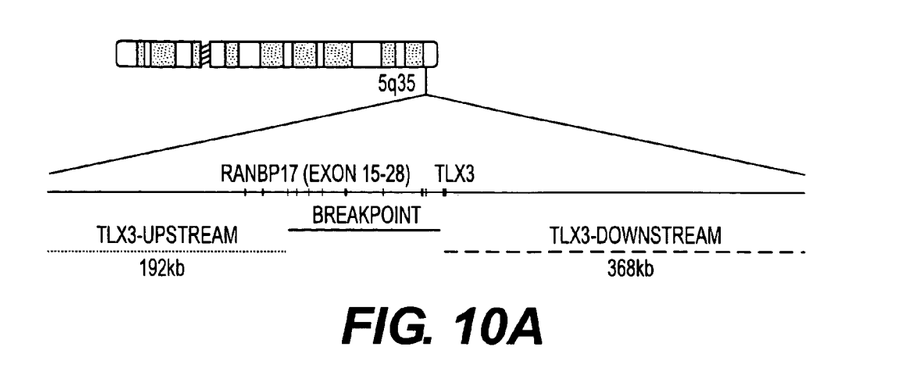
Figure 10B:
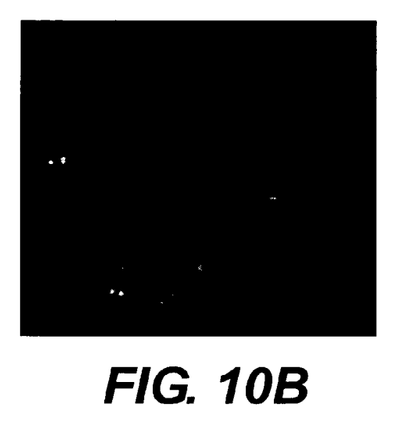
Figure 10C:
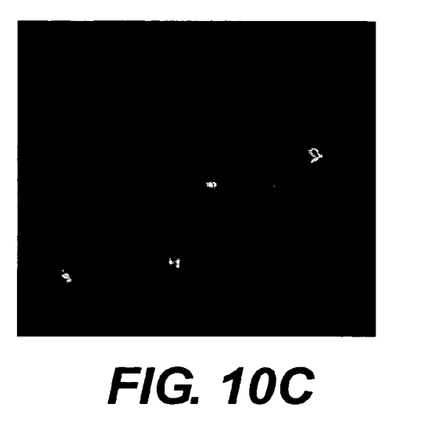
Figure 10D:
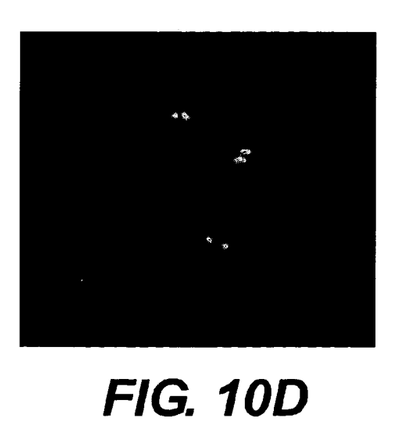
Figure 10E:
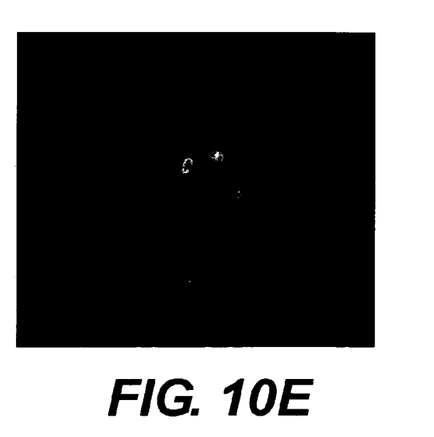

On each target area, 10 μL of DNA Hybridization Buffer (100 ng fluorescein labeled probe, 100 ng Texas Red labeled probe, 100 ng AMCA (7-amino-4-methylcoumarin-3-acitic acid) labeled probe, 5 μM PNA Oligo Mix, 45% formamide, 300 mM NaCl, 5 mM $NaPO_4$, 10% Dextran sulphate) is added and an 18×18 mm coverslip is applied to cover the hybridization area on the slides. The edges of the coverslip are sealed with rubber cement before denaturation at 82° C. for 5 minutes. The slides are hybridized overnight at 45° C. After hybridization, the coverslip is removed and the slides are washed for 10 minutes in a stringent wash buffer (0.2×SSC, 0.1% Triton X-100) at 65° C. Blocking DNA may also be added as shown in FIG. 5 to avoid unwanted binding.

The slides are then rinsed in TBS for 1 minute before they are dehydrated in a cold (4° C.) series of 70%, 85% and 96% ethanol as described above. Each slide is mounted with 10 μL of anti-fade solution (Vectashield H-1000, Vector Laboratories, Inc. Burlingame) supplemented with 0.1 µg/mL 4,6-diamidino-2-phenylindole (DAPI, Sigma Chemicals) and sealed with a coverslip.

The slides are analyzed using a fluorescence microscope equipped with a CCD digital camera. In the slide containing a normal cell chromosome preparation, the Texas Red labeled probe and the FITC labeled probe co-localize on both sister chromatids to produce two identical fused signals. See FIG. 3. The AMCA labeled probe does not co-localize with either the Texas Red labeled probe or the FITC labeled probe. In the abnormal cell chromosome preparation, the original Texas Red/FITC signal remains on one chromatid. But on the other chromatid, only one of the labels remains (i.e., FITC) while the other label (Texas Red) has co-localized with the AMCA label on another chromosome to form a new fused Texas Red/AMCA signal. See FIG. 3. The loss of an original fused signal and the emergence of a new fused signal in the test sample preparation indicates a change in chromosomal structure.

Example 3

PDGFRA probes were hybridized to metaphase chromosomes from metaphase spreads from normal tissue and from the cell line ELO-1. A normal PDGFRA locus on chromosome 4 was detected in normal cells as either a yellow dot or by co-localized green/red signals due to the juxtaposition of the red probes and green probes hybridizing to regions upstream and downstream from an anticipated disease-related change in chromosomal structure. An additional chromosome 4 was also detected as a result of an amplification of the derivative chromosome 4.

Example 4

PDGRFB probes were hybridized to metaphase chromosomes from the NALM-6 cell line. A normal PDGFRB locus on chromosome 5 was detected in normal cells as either a yellow dot or by co-localized green/red signals due to the juxtaposition of the red probes and green probes hybridizing to regions upstream and downstream from an anticipated disease-related change in chromosomal structure. Lack of one green signal indicated a deletion of the derivative chromosome 5, while a red signal indicated a translocation to another chromosome.

Example 5

Other probes have been designed to bind to the BCL2, BCL3, BCL6, BCL10, MALT1, MYC, PAX5, CCND1, TLX1, TCRAD, TCRB, and TCRG genes. Those probes may be used to detect changes in chromosomal structure or target areas involved in a variety of diseases, such as T-cell prolymphocytic leukemia, T-cell large granular lymphocyte leukemia (T-LGL), hypereosinophilic syndrome (HES), Anaplastic large cell lymphoma (ALCL), Lymphoplasmocytic lymphoma(LPL), burkitt's lymphoma (BL), mantle cell lymphoma (MCL), Splenic marginal zone lymphoma (SMZL), Marginal zone (MALT), Follicular lymphoma (FL), Diffuse large cell lymphoma (DLBCL), T-cell leukemia/lymphoma (TLL), T-cell leukemia/lymphoma (TLL), and lymphoma.

Specific probe sequences that may be used in this technique are provided in an accompanying United States application entitled "Nucleic Acid Probes and Nucleic Acid Analog Probes," as well as in U.S. Provisional Application No. 60/567,570, filed May 4, 2004, to which this application claims priority. Both of those applications are incorporated herein by reference.

Other embodiments of the invention will be apparent to those skilled in the art from consideration of the specification and practice of the invention disclosed herein. It is intended that the specification and examples be considered as exemplary only. All references either discussed or referred to herein are incorporated by reference.

What is claimed is:

1. A method for detecting a change in a target area comprising:
    (a) obtaining a preparation of nucleic acids;
    (b) contacting a first probe containing a first label with a complementary probe having a nucleotide sequence complementary to a non-target sequence which may be present in the preparation of nucleic acids to form a bound labeled probe;
    (c) removing the bound labeled probe leaving a first selected probe;
    (d) contacting the preparation of nucleic acids with the first selected probe;
    (e) contacting the preparation of nucleic acids with a second probe containing a second label, wherein the first selected probe and the second probe bind within the same target area in a normal control sample, and wherein the binding of the first selected probe and second probe results in a fused signal in a normal control sample;
    (f) contacting the preparation of nucleic acids with a third probe containing a third label, wherein the third probe binds other nucleic acids or another region of the same nucleic acid in the preparation of nucleic acids; and
    (g) detecting a change in nucleic acid structure,
        wherein the first selected probe and the second probe are not present on the same target area resulting in a split signal; and
        wherein
            (i) the first selected probe and the third probe; or
            (ii) the second probe and the third probe are present on the same target area resulting in a new fused signal.

2. A method for detecting a change in chromosomal structure comprising:
    (a) obtaining a preparation of chromosomes;
    (b) contacting the preparation of chromosomes with a first probe containing a first label;
    (c) contacting the preparation of chromosomes with a second probe containing a second label, wherein the first probe and the second probe bind the same chromosome in a normal control sample, and wherein the binding of the first probe and second probe results in a fused signal in the normal control sample;
    (d) contacting the preparation of chromosomes with a third probe containing a third label, wherein the third probe binds other chromosomes or another region of the same chromosome in the preparation of chromosomes; and
    (e) detecting the change in chromosomal structure,
        wherein the first probe and the second probe are not present on the same chromosome resulting in a split signal; and
        wherein
            (i) the first probe and the third probe; or
            (ii) the second probe and the third probe
        are present on the same chromosome resulting in a new fused signal; and wherein (f) prior to contacting the nucleic acid preparation with the probes,
(i) binding one or more of the first probe containing the first label, the second probe containing the second label, and the third probe containing the third label, to a complementary probe, the complementary probe having a nucleotide sequence complementary to a non-target sequence which may be present in the chromosome sample, to create a bound labeled probe; and
(ii) removing the bound labeled probe.

3. The method of claim 2, wherein one probe is treated according to step (f).

4. The method of claim 2, wherein two of the probes are treated according to part (f).

5. The method of claim 2, wherein all three probes are treated according to part (f).

6. The method of claim 2, wherein the complementary probe is attached to a solid surface.

7. The method of claim 6, wherein the solid surface is a bead or a slide.

8. The method of claim 2, wherein the change in chromosomal structure is chosen from at least one of aneuploidy, amplification, deletion, fusion, translocation, duplication, insertion, and inversion.

9. The method of claim 2, wherein the first probe, the second probe, or the third probe, or more than one of said probes, is a nucleic acid probe.

10. The method of claim 9, wherein the nucleic acid probe is comprised of DNA or RNA.

11. The method of claim 2, wherein the complementary probe is a non-nucleic acid probe.

12. The method of claim 11, wherein the non-nucleic acid probe is comprised of PNA or LNA.

13. The method of claim 2, wherein the first probe, the second probe, or the third probe, or more than one of said probes, is a non-nucleic acid probe.

14. The method of claim 13, wherein the non-nucleic acid probe is comprised of PNA or LNA.

15. The method of claim 2, wherein the labels are chosen from at least one chromophore, fluorochrome, spin label, radioisotope, enzyme, hapten, Quantum Dot, bead, aminohexyl, pyrene, and chemiluminescent compound.

16. The method of claim 15, wherein the fluorochrome is chosen from at least one of 5(6)-carboxyfluorescein, cyanine dyes, (diethyl-amino)coumarin, fluorescein, tetramethylrhodamine, lissamine, Texas Red, AMCA, TRITC, IR dyes, Dyomics dyes, phycoerythrine, cascade blue, Oregon green 488, pacific blue, rhodamine green, and Alexa dyes.

17. The method of claim 15, wherein the hapten is chosen from at least one of 5(6)-carboxyfluorescein, 2,4-dinitrophenyl, digoxigenin, rhodamine, bromodeoxy uridine, sulfonate, acetylaminoflurene, mercury trintrophonol, estradiol, and biotin.

18. The method of claim 15, wherein the enzyme is chosen from at least one of soybean peroxidase, alkaline phosphatase, and horseradish peroxidase.

19. The method of claim 15, wherein the chemiluminescent compound is acridinium.

20. The method of claim 2, wherein the fused signals are detected by a color change.

21. The method of claim 2, wherein the split signal is detected by a color change.

22. The method of claim 2, wherein the first probe and the second probe bind on either side of a suspected break point in the chromosome.

23. The method of claim 2, wherein at least two probes contact the chromosome preparation simultaneously.

24. The method of claim 2, wherein the first probe, the second probe, and the third probe contact the chromosome preparation simultaneously.

* * * * *